(12) United States Patent
Stromgren et al.

(10) Patent No.: US 8,236,555 B2
(45) Date of Patent: Aug. 7, 2012

(54) MULTIPLEXED ASSAY METHODS

(75) Inventors: Selen A. Stromgren, Rockville, MD (US); Eli N. Glezer, Chevy Chase, MD (US)

(73) Assignee: Meso Scale Technologies, LLC, Gaithersburg, MD (US)

( * ) Notice: Subject to any disclaimer, the term of this patent is extended or adjusted under 35 U.S.C. 154(b) by 234 days.

(21) Appl. No.: 12/720,412

(22) Filed: Mar. 9, 2010

(65) Prior Publication Data

US 2010/0159490 A1    Jun. 24, 2010

Related U.S. Application Data

(62) Division of application No. 11/249,077, filed on Oct. 12, 2005, now Pat. No. 7,704,730.

(60) Provisional application No. 60/618,713, filed on Oct. 14, 2004.

(51) Int. Cl.
*C12M 1/34* (2006.01)
*C12M 3/00* (2006.01)

(52) U.S. Cl. .................. 435/287.9; 435/7.1; 435/283.1; 435/287.1; 435/287.2; 435/288.7; 435/288.3; 436/807; 436/809; 436/518; 436/166; 436/172; 422/50; 422/407; 422/68.1

(58) Field of Classification Search .................. 435/7.1, 435/283.1, 287.1, 287.2, 287.9, 288.7, 288.32; 436/518, 524, 525, 526, 164, 166, 172, 807, 436/809; 422/50, 407, 68.1
See application file for complete search history.

(56) References Cited

U.S. PATENT DOCUMENTS

| | | | |
|---|---|---|---|
| 5,045,451 A | 9/1991 | Uhr et al. | |
| 5,486,452 A | 1/1996 | Gordon et al. | |
| 6,281,004 B1 * | 8/2001 | Bogen et al. | ................ 435/287.1 |
| 6,905,816 B2 * | 6/2005 | Jacobs et al. | ...................... 435/5 |
| 2003/0204331 A1 | 10/2003 | Whitney et al. | |
| 2004/0022677 A1 | 2/2004 | Wohlstadter et al. | |
| 2005/0277682 A1 | 12/2005 | Licari et al. | |

* cited by examiner

*Primary Examiner* — Melanie J Yu
(74) *Attorney, Agent, or Firm* — Scully, Scott, Murphy & Presser, P.C.

(57) ABSTRACT

The present invention is directed to methods for conducting multiplexed assays. The methods are particularly well suited for measuring a plurality of analytes that may be present in very different abundances. The invention also relates to systems, devices, equipment, kits and reagents for use in such methods.

20 Claims, 1 Drawing Sheet

MULTIPLEXED ASSAY METHODS

CROSS REFERENCES TO RELATED APPLICATIONS

The present application is a divisional of application Ser. No. 11/249,077 filed on Oct. 12, 2005, now U.S. Pat. No. 7,704,730, which claims priority to U.S. Provisional Application No. 60/618,713, filed Oct. 14, 2004.

FIELD OF THE INVENTION

The present invention is directed to methods for conducting multiplexed assays. The methods are particularly well suited for measuring a plurality of analytes that may be present in very different abundances. The invention also relates to systems, devices, equipment, kits and reagents for use in such methods.

BACKGROUND OF THE INVENTION

Binding assays generally have a range of analyte concentrations, the dynamic range, for which the reported signal is dependent upon the amount of analyte present. Where the amount of analyte exceeds the dynamic range of the assay, saturation of binding sites occurs and the reported signal is not indicative of the true analyte concentration. Likewise, when the amount of analyte present in the sample falls below the lower threshold of the assay's dynamic range, the assay is insufficiently sensitive to the actual analyte concentration, and the reported signal will also not be indicative of the true analyte concentration.

Two approaches have conventionally been employed in single measurement assays for analytes having concentrations above the upper limit of the dynamic range of the assay: (1) diluting the sample to reduce the concentration to within the assay range; and (2) reducing the binding reaction time to prevent saturation of binding sites. In the first approach, multiple dilutions of a sample are sometimes made and individually tested so as to increase the likelihood that one of the dilutions is within the dynamic range of the assay. In the second approach, multiple experiments can be carried out using different binding reaction times so as to increase the likelihood that one of the experiments has a binding reaction time that produces an assay signal within the dynamic range of the assay.

It is increasingly desirable to assay multiple different analytes simultaneously in the same sample. Multiplexing permits greater throughput, minimizes sample volume and handling, provides internal standardization control, decreases assay cost and increases the amount of information that is obtainable from each sample. Various approaches for conducting multiplexed assays have been described. For example, multiplexed testing is described in U.S. patent application Ser. Nos. 10/185,274 and 10/185,363, both filed on Jun. 28, 2002, entitled "Assay Plates, Reader Systems and Methods For Luminescence Test Measurements," published as U.S. Publ. No. 20040022677, U.S. patent application Ser. No. 10/238,960, filed Sep. 10, 2002, entitled "Methods, Reagents, Kits and Apparatus for Protein Function," published as US Pat. Pub. No. 20030207290, U.S. patent application Ser. No. 10/238,391, filed Sep. 10, 2002, entitled "Methods and apparatus for conducting multiple measurements on a sample"; published as US Pat. Publ. No. 20030113713, Provisional U.S. Patent Application No. 60/517,606, filed on Nov. 4, 2003, entitled "Modular Assay Plates, Reader System and Methods For Test Measurements"; and U.S. patent application Ser. No. 10/744,726, filed on Dec. 23, 2003, entitled "Assay Cartridges and Methods of Using Same", each of which is incorporated by this reference. One approach to multiplexing binding assays involves the use of patterned arrays of binding reagents (see, e.g., U.S. Pat. Nos. 5,807,522 and 6,110,426, both entitled "Methods for Fabricating Microarrays of Biological Samples" issued Sep. 15, 1998 and Aug. 29, 2000 respectively, Delehanty J B, Printing functional protein microarrays using piezoelectric capillaries, *Methods Mol Biol.* (2004) 278:135-44; Lue Y, Chen Y, Zhu Q, Lesaicherre L, Yao S Q, Site-specific immobilization of biotinylated proteins for protein microarray analysis, *Methods Mol Biol.* (2004) 278:85-100; Lovett, Toxicogenomics: Toxicologists Brace for Genomics Revolution, *Science* (2000) 289: 536-537; Berns A., Cancer: Gene expression in diagnosis, *Nature* (2000) 403, 491-492; Walt, Molecular Biology: Bead-based Fiber-Optic Arrays, *Science* (2000) 287: 451-452. Another approach involves the use of binding reagents coated on beads that can be individually identified and interrogated. International Patent publication WO9926067A1 (Watkins et al.) describes the use of magnetic particles that vary in size to assay multiple analytes; particles belonging to different distinct size ranges are used to assay for different analytes. The particles are designed to be distinguished and individually interrogated by flow cytometry. Vignali has described a multiplex binding assay in which 64 different bead sets of microparticles are employed, each having a uniform and distinct proportion of two dyes (Vignali, D. A. A., "Multiplexed Particle-Based Flow Cytometric Assays," *J. Immunol. Meth.* (2000) 243:243-255). A similar approach involving a set of 15 different beads of differing size and fluorescence has been disclosed as useful for simultaneous typing of multiple pneumococcal serotypes (Park, M. K. et al., "A Latex Bead-Based Flow Cytometric Immunoassay Capable Of Simultaneous Typing Of Multiple Pneumococcal Serotypes (Multibead Assay)," *Clin Diagn Lab Immunol.* (2000) 7:486-9). Bishop, J. E. et al. have described a multiplex sandwich assay for simultaneous quantification of six human cytokines (Bishop, J. E. et al., "Simultaneous Quantification of Six Human Cytokines in a Single Sample Using Microparticle-based Flow Cytometric Technology," *Clin Chem.* (1999) 45:1693-1694).

A significant complexity arises in conducting multiplexed assays, however, from the fact that the individual analytes may occur in widely different abundance. As a consequence, it may not always be possible to find a single set of conditions (e.g., sample dilution or binding reaction time) which bring all analytes of interest within the assay's dynamic range. An appropriate dilution level for a high concentration analyte, for example, may leave the low concentration analyte undetectable.

SUMMARY OF THE INVENTION

The invention relates to methods for conducting multiplexed assays. The invention broadly relates to methods of measuring two or more analytes in a sample using portions of the sample which have been processed differently, (e.g., portions that have diluted to different extents, diluted with different diluents, combined with different modification and/or detection reagents, exposed to different temperatures, exposed to different enzymes, etc. . . . ). The methods are particularly well suited for measuring a plurality of analytes that may be present in very different abundances. The methods are also well suited for conducting multiplexed assays for a plurality of analytes, where the analytes have different affinities to binding reagents used in the assays and/or the assays for each of the analytes have different sensitivities. The methods also have specific advantages where the detection reagents for two or more analytes are incompatible.

The invention relates to a method for measuring analytes in a sample comprising: i) contacting a first portion of the sample with one or more binding surfaces; ii) contacting the binding surface(s) with a first detection reagent that binds to the first analyte; iii) contacting a second portion of the sample with the binding surface(s); iv) contacting the binding surface(s) with a second detection reagent that binds to the second analyte; and v) measuring the amount of the first detection reagent and the second detection reagent bound to the binding surface(s). The first and second portions of the sample may have been processed differently as described above. In one embodiment, the first and second detection reagents are measured, preferably simultaneously, after both the first and second portions have contacted the binding surface(s). Advantageously, the measurement step (i.e., the step involving the measurement of the first and second detection reagents (e.g., step (v)) may occur in a single volume or measurement chamber (e.g., a single well of a multi-well plate, a single channel of a cartridge, a single mixture of beads, etc.).

The first and second portions may be diluted to different extents relative to the original sample. The times of contact of the first and second portions with the binding surface(s) may be different. Advantageously, the dilution factors and/or contact times are selected to increase the likelihood that the concentrations of the first and second analyte in a sample fall within the dynamic ranges for their respective assays.

One method according to this aspect of the invention comprises: i) contacting a first of the sample with one or more binding surfaces, ii) immobilizing an amount of a first analyte in the first dilution on the binding surface(s), iii) binding a first detection reagent to the first analyte immobilized on the binding surface(s), iv) contacting a second portion of the sample with one or more binding surfaces, wherein the second portion has different properties or characteristics and/or has been subjected to different processing (e.g., different diluent, reagents, etc.) compared to the first portion, v) immobilizing an amount of a second analyte in the second dilution on the binding surface(s), vi) binding a second detection reagent to the second analyte immobilized on the surface(s), and vii) measuring the amounts of the first detection reagent and second detection reagent bound to the binding surface(s).

Advantageously, the measurement step (i.e., the step involving the measurement of the first and second detection reagents (e.g., step (vii)) may occur in a single volume or measurement chamber.

The first portion of the sample may be processed differently from the second portion of the sample. The first portion of the sample maybe diluted with a diluent different from the diluent in the second dilution or the first and second portions may be diluted to different extents. One or both portions of the sample may have been treated with detergents, lipids, blocking proteins, modification reagents and/or enzymes. One or both portions of the sample may have been subjected to different temperatures or other environmental conditions. Advantageously, the methods of the invention allow the processing of each portion to be optimized for the measurement of a specific analyte in the sample and also allow for the use of processing conditions that may be detrimental to the measurement of other analytes of interest in the sample.

In one aspect of the invention, the first portion may be diluted to create the first dilution of the sample and the second portion maybe diluted to create the second dilution of the sample. The first portion may be more dilute (i.e., has a greater dilution factor) than the second portion. Optionally, the second portion is an undiluted aliquot of the sample. The methods may be used to analyze samples containing substantially higher concentrations of the first analyte relative to the second analyte.

Thus, the invention relates to a method for measuring analytes in a sample comprising: i) contacting a first dilution of the sample with one or more binding surfaces having binding reagents that bind a first analyte and a second analyte; ii) contacting the binding surface(s) with a first detection reagent that binds to the first analyte; iii) contacting a second dilution of the sample with the binding surface(s); iv) contacting the binding surface(s) with a second detection reagent that binds to the second analyte; and v) measuring the amount of the first detection reagent and the second detection reagent bound to the binding surface(s). In one embodiment, the first and second detection reagents are measured, preferably simultaneously, after both the first and second dilutions have contacted the binding surface(s). Advantageously, the measurement step (i.e., the step involving the measurement of the first and second detection reagents (e.g., step (v)) may occur in a single volume or measurement chamber.

The invention also relates to a method for measuring analytes in a sample comprising: i) contacting a first dilution of the sample with one or more binding surfaces, ii) immobilizing an amount of a first analyte in the first dilution on the binding surface(s), iii) binding a first detection reagent to the first analyte immobilized on the binding surface(s), iv) contacting a second dilution of the sample with one or more binding surfaces, wherein the second dilution has a dilution factor lower than the first dilution, v) immobilizing an amount of a second analyte in the second dilution on the binding surface(s), vi) binding a second detection reagent to the second analyte immobilized on the surface(s), and vii) and measuring the amounts of the first detection reagent and the second detection reagent bound to the binding surface(s). In one embodiment, the first and second detection reagents are measured, preferably simultaneously, after both the first and second dilutions have contacted the binding surface(s). Advantageously, the measurement step (i.e., the step involving the measurement of the first and second detection reagents (e.g., step (vii)) may occur in a single volume or measurement chamber.

The invention also relates to a method for measuring analytes in a sample comprising: i) contacting a first dilution of the sample with one or more binding surfaces; ii) contacting the binding surface(s) with a first detection reagent, wherein a) the binding surface(s) and the first detection reagent bind a first analyte; or b) the binding surface(s) binds the first analyte and the first detection reagent competes with the first analyte for the binding surface(s); or c) the first binding reagent binds the first analyte and the binding surface(s) competes with the first analyte for binding to the first detection reagent; iii) contacting a second dilution of the sample with the binding surface(s); iv) contacting the binding surface(s) with a second detection reagent, wherein a) the binding surface(s) and the second detection reagent bind the second analyte; or b) the binding surface(s) binds the second analyte and the second detection reagent competes with the second analyte for the binding surface(s), or c) the second binding reagent binds the second analyte and the binding surface(s) competes with the second analyte for binding to the second detection reagent; and v) measuring the amount of the first detection reagent and the second detection reagent bound to the binding surface(s). In one embodiment, the first and second detection reagents are measured, preferably simultaneously, after both the first and second dilutions have contacted the binding surface(s).

Advantageously, the measurement step (i.e., the step involving the measurement of the first and second detection reagents (e.g., step (v)) may occur in a single volume or measurement chamber.

In one embodiment, the first dilution is more dilute (i.e., has a greater dilution factor) than the second dilution. Optionally, the second dilution is an undiluted aliquot of the sample. In an alternative embodiment, the contact time for the second dilution with the binding surface(s) is longer (e.g., by a factor of 5, 10, 100, 1,000, or 10,000) than the contact time for the first dilution. The methods may be used to analyze samples containing substantially higher concentrations of the first analyte relative to the second analyte.

The methods of the invention, as described above, may further comprise washing unbound first detection reagent away from the binding surface(s) prior to contacting the binding surface(s) with the second dilution of the sample. Advantageously, washing unbound first detection reagent away from the binding surface(s) also removes the diluent of the first dilution. Optionally, the unbound sites for the first analyte on the binding surface(s) are blocked after contacting said binding surface(s) with the first dilution of the sample but prior to contacting the binding surface(s) with the second dilution of said sample. Such blocking may be provided by blocking reagents in a wash solution used to wash the binding surface(s).

In certain embodiments of the invention, the first detection reagent is labeled with a first label and the second detection reagent is labeled with a second label. The first label and the second label are measurably distinct and can be individually measured. The detection reagents are, preferably, labeled with a label selected from the group consisting of electrochemiluminescent (ECL) labels, chemiluminescent labels, fluorescent labels, phosphorescent labels, radioactive labels, enzyme labels, electroactive labels, quantum dots, magnetic labels and light scattering labels.

Preferably, the first dilution is diluted (relative to the sample) by a factor of at least 5, 10, 100, 1000, or 10000. The second dilution is less dilute than the first dilution and may be an undiluted portion of the sample.

The binding surfaces (or binding domains on a binding surface) may comprise at least one binding reagent immobilized thereon that may bind to an analyte of interest. The binding surface(s) of the invention may comprise two or more discrete binding domains including a first binding domain comprising the first binding reagent and a second binding domain comprising the second binding reagent. In one embodiment, the binding domains are patterned on a binding surface. In an alternate embodiment, the first binding domain is on a first particle (or set of particles) and the second binding domain is on a second particle (or set of particles).

The binding of the analyte of interest to the binding reagent on the surface may be direct or may occur via one or more bridging reagents. Accordingly, the assay methods of the invention may include contacting the sample with a bridging reagent that binds both the binding reagent immobilized on the binding surface and an analyte.

The term binding surface encompasses a wide range of solid phase supports. The binding surfaces may be formed on the surface of a variety of structures, such as electrodes, wells of a multi-well plate, electrodes integrated into a multi-well plate, microparticles (including magnetic microparticles and latex microparticles), cuvettes, glass or polymer slides, porous membranes, etc.

DETAILED DESCRIPTION OF THE INVENTION

Figure 1:
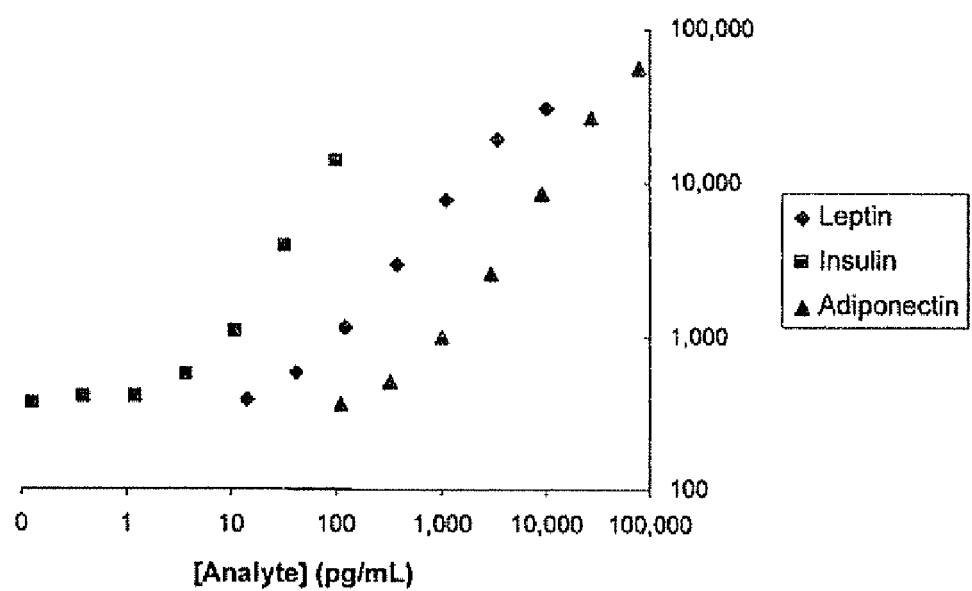
FIG. 1 shows the results of a multiplexed electrochemiluminescence (ECL) assay for mouse insulin, leptin and adiponectin. The plot shows ECL signal (vertical axis) for each analyte concentration (horizontal axis).

The invention relates to methods for conducting multiplexed assays. The methods can be used for measuring two or more analytes having different characteristics or properties (e.g., abundances, affinities, etc.) or requiring different processing (e.g., use of different diluents, incompatible reagents or processing steps, etc.).

The invention relates to methods of measuring two or more analytes in a sample by splitting a sample into two or more portions. In one aspect of the inventions, portions of the sample have different dilutions (e.g., different diluents and/or different dilution ratios). The methods are particularly well suited for measuring a plurality of analytes that may be present in very different abundances.

The methods are also well suited for conducting multiplexed assays for a plurality of analytes, where analytes have different affinities to binding reagents used in the assays and/or assays for each of the analytes have different sensitivities. The methods also have specific advantages where detection reagents used in the measurement of two or more analytes are incompatible.

The invention relates to a method for measuring analytes in a sample comprising: i) contacting a first portion of the sample with one or more binding surfaces; ii) contacting the binding surface(s) with a first detection reagent that binds to the first analyte; iii) contacting a second portion of the sample with the binding surface(s); iv) contacting the binding surface(s) with a second detection reagent that binds to the second analyte; and v) measuring the amount of the first detection reagent and the second detection reagent bound to the binding surface(s). The first and second portions of the sample may be subjected to different treatment. In one embodiment, the first and second detection reagents are measured, preferably simultaneously, after both the first and second dilutions have contacted the binding surface(s). Advantageously, the measurement step (i.e., the step involving the measurement of the first and second detection reagents (e.g., step (v)) may occur in a single volume or measurement chamber (e.g., a single well of a multi-well plate, a single channel of a cartridge, a single mixture of beads, etc.).

One method according to this aspect of the invention comprises: i) contacting a first portion of the sample with one or more binding surfaces, ii) immobilizing an amount of a first analyte in the first dilution on the binding surface(s), iii) binding a first detection reagent to the first analyte immobilized on the binding surface(s), iv) contacting a second portion of the sample with one or more binding surfaces, wherein the second portion has different properties or characteristics and/or has been subjected to different processing (e.g., different diluent, reagents, etc.) compared to the first portion, v) immobilizing an amount of a second analyte in the second dilution on the binding surface(s), vi) binding a second detection reagent to the second analyte immobilized on the surface(s), and vii) and measuring the amounts of the first detection reagent and the second detection reagent bound to the binding surface(s). Advantageously, the measurement step (i.e., the step involving the measurement of the first and second detection reagents (e.g., step (vii)) may occur in a single volume or measurement chamber.

The first portion of the sample may be processed differently from the second portion of the sample. The first portion of the sample maybe diluted with a diluent different from the diluent in the second dilution or the first and second portions may be diluted to different extents. One or both portions of the sample may have been treated with detergents, lipids, blocking proteins, modification reagents and/or enzymes. One or both of the sample may have been subjected to different temperatures or other environmental conditions. Advantageously, the methods of the invention allow the processing of each portion to be optimized for the measurement of a specific analyte in the sample and also allow for the use of processing conditions that may be detrimental to the measurement of other analytes of interest in the sample. By way of example, a first portion of an analyte may be formulated and/or treated so as to optimize the presentation of a first analyte to its corresponding binding partner. This optimization may include, for example, chemical modification of the analyte with one or more modifying reagents (e.g., acetylation, methylation, etc.), removal of chemical modifications (e.g., dephosphorylation, deacetylation, etc.), release of the analyte from binding complexes present in the sample, proteolysis, etc. The formulation and/or treatment may be incompatible with the measurement of a second analyte in the sample; this second analyte is measured from a second portion of the sample that is formulated/treated in an appropriate manner for measuring the second analyte.

In one aspect of the invention, the first portion may be diluted to create a first dilution of the sample and the second portion maybe diluted to create a second dilution of the sample. The first portion may be more dilute (i.e., has a greater dilution factor) than the second portion. Optionally, the second portion is an undiluted aliquot of the sample. In another aspect of the invention, the contact time for the second dilution with the binding surface(s) is longer (e.g., by a factor of 5, 10, 100, 1,000, or 10,000) than the contact time for the first dilution. The methods may be used to analyze samples containing substantially higher concentrations of the first analyte relative to the second analyte.

Preferably, the methods utilize two or more dilutions of a sample. According to one embodiment, preparation of a first dilution of a sample comprises combining a first portion of the sample with a diluent. The first dilution has a first dilution factor selected to bring the concentration of a first analyte (or group of analytes) in the sample to within the dynamic range of the assay. The dilution factor, as used herein, refers to the ratio of the total volume of the diluted sample to the initial volume of the portion of the sample being diluted. The dilution factor will, therefore, also correspond to the ratio of the concentration of an analyte in the original sample to the concentration of the analyte in the diluted sample. The first dilution factor may be, e.g., greater than 1, 10, 100, 1,000 or 10,000. A second dilution of the sample is also prepared having a second dilution factor selected to bring to bring the concentration of a second less abundant analyte (or group of analytes) in the sample to within the dynamic range of the assay. The dilution factor of the second dilution is less than the first dilution factor. The second dilution factor may be, e.g., more than 10, 100, 1000, or 10,000 times less than the first dilution factor. In one preferred embodiment, the second dilution factor is unity (i.e., an undiluted portion of the sample is analyzed). Additional dilutions of portions of the sample may be carried out as necessary to bring the concentrations of additional analytes (or groups of analytes) to within the dynamic range of the assay. In another aspect, the second dilution and/or any additional dilution utilized a diluent different from a diluent utilized in the first, and/or previous, dilution. In one embodiment of the invention the first and the second diluents are each optimized for the measurement of different analytes.

In one embodiment, the method is a binding assay. In another embodiment, the method is a solid-phase binding assay (e.g., a solid phase immunoassay) and comprises contacting an assay composition with one or more binding surfaces that bind analytes of interest (or their binding competitors) present in the assay composition. The method may also include contacting the assay composition with one or more detection reagents capable of specifically binding with the analytes of interest. The multiplexed binding assay methods according to preferred embodiments of the invention can involve a number of formats available in the art. Suitable assay methods include sandwich or competitive binding assays format. Examples of sandwich immunoassays are described in U.S. Pat. No. 4,168,146 to Grubb et al. and U.S. Pat. No. 4,366,241 to Tom et al., both of which are incorporated herein by reference. Examples of competitive immunoassays include those disclosed in U.S. Pat. No. 4,235,601 to Deutsch et al., U.S. Pat. No. 4,442,204 to Liotta, and U.S. Pat. No. 5,208,535 to Buechler et al., all of which are incorporated herein by reference.

One embodiment of the invention is a solid phase binding assay method for measuring analytes in a sample. According to this embodiment, a first dilution of the sample is contacted with one or more binding surfaces and a first analyte is bound to one or more binding surfaces and measured. Then a second dilution of the sample is contacted with the same binding surface(s), and a second analyte is bound to the surface(s) and measured. The binding surfaces may advantageously have binding reagents that bind the first analyte and a second analyte. Optionally, the first and second analytes are measured, preferably simultaneously, after the binding surface(s) are contacted with both the first and second detection reagents. Alternatively, the analytes are measured by measuring their intrinsic characteristics, for example, mass, intrinsic fluorescence, phosphorescence, etc. . . .

Accordingly, the invention includes a method for measuring analytes in a sample comprising:
a) contacting a first dilution of the sample with one or more binding surfaces;
b) measuring a first analyte bound on said surface(s);
c) contacting a second dilution of the sample with the same binding surface(s);
d) measuring a second analyte bound on said surface(s).

Advantageously, the second dilution may have a dilution factor less than the first dilution and/or use a diluent different than the diluent used in the first dilution. Also, advantageously, the measurement steps (i.e., the step involving the measurement of the first and second analytes (e.g., steps (b) and (d)) may occur in a single volume or measurement chamber.

One embodiment of the invention is a solid phase binding assay method for measuring analytes in a sample. According to this embodiment, a first dilution of the sample is contacted with one or more binding surfaces and a first analyte is bound to one or more binding surfaces and measured. Then a second dilution of the sample, having a dilution factor less than the first dilution, is contacted with the same binding surface(s), and a second analyte is bound to the surface(s) and measured. The binding surfaces may advantageously have binding reagents that bind the first analyte and a second analyte. Optionally, the first and second analytes are measured after the binding surface(s) are contacted with both the first and second detection reagents. Alternatively, the analytes are measured by measuring their intrinsic characteristics, for example, mass, intrinsic fluorescence, phosphorescence, etc. . . . Also, advantageously, the measurement steps (i.e., the step involving the measurement of the first and second analytes may occur in a single volume or measurement chamber.

Accordingly, the invention includes a method for measuring analytes in a sample comprising:
  a) contacting a first dilution of the sample with one or more binding surfaces;
  b) measuring a first analyte bound on said surface(s);
  c) contacting a second dilution of the sample with the same binding surface(s), the second dilution having a dilution factor less than the first dilution;
  d) measuring a second analyte bound on said surface(s).

Another embodiment of the invention is a solid phase binding assay method for measuring analytes in a sample. According to this embodiment, a first dilution of the sample is contacted with one or more binding surfaces having binding reagents that bind the first analyte and the first analyte is bound to one or more of the binding surfaces. Then the surface(s) is contacted with a blocking reagent that binds to the binding reagents specific to the first analyte, thereby blocking binding reagents which are specific to the first analyte but are not bound to the first analyte. Then a second dilution of the sample, having a dilution factor less than the first dilution, is contacted with the same binding surface(s) and the second analyte is bound to the surface(s). Then both the first and the second analytes are measured. Advantageously, the first and the second analytes may be measured simultaneously. Optionally, the first and second analytes are measured after the binding surface(s) are contacted with first and second detection reagents that bind the first and second analytes, respectively. The amount of the bound analytes is determined via measurement of the amount of bound detection reagents. Alternatively, the analytes are measured by measuring an intrinsic characteristic of the analytes, for example, mass, intrinsic fluorescence, phosphorescence, etc. . . .

Accordingly, the invention includes a method for measuring analytes in a sample comprising:
  a) contacting a first dilution of the sample with one or more binding surfaces having binding reagents that bind a first analyte and a second analyte;
  b) contacting said binding surface(s) with a blocking reagent, wherein said blocking reagents binds to said binding reagents that bind said first analyte;
  c) contacting a second dilution of the sample with the same binding surface(s), the second dilution having a dilution factor less than the first dilution; and
  d) measuring said first analyte and said second analyte bound on said surface(s).

Advantageously, the measurement step (i.e., the step involving the measurement of the first and second analytes (e.g., step (d)) may occur in a single volume or measurement chamber.

One embodiment of the invention is a solid phase binding assay method for measuring analytes in a sample. According to this embodiment, a first dilution of the sample is contacted with binding reagents immobilized on one or more binding surfaces, the binding reagents binding analytes present in the sample including a first and second analytes. Then the binding surface(s) are contacted with a first detection reagent which binds to the first, preferably more abundant, analyte or analytes. Then a second dilution of the sample, having a dilution factor less than the first dilution, is contacted with the same binding surface(s). The binding surface(s) are further contacted with a second detection reagent which binds to the second, preferably less abundant, analyte or analytes. The first detection reagent and the second detection reagents bound to the binding surface(s) are measured, preferably after the binding surface(s) are contacted with the first and second detection reagents, and more preferably simultaneously.

Accordingly, the invention includes a method for measuring analytes in a sample comprising:
  a) contacting a first dilution of the sample with one or more binding surfaces having binding reagents that bind a first analyte and a second analyte;
  b) contacting these binding surface(s) with a first detection reagent, wherein the first detection reagent binds to the first analyte;
  c) contacting a second dilution of the sample with the same binding surface(s), the second dilution having a dilution factor less than the first dilution;
  d) contacting the binding surface(s) with a second detection reagent, wherein the second detection reagent binds to the second analyte; and
  e) measuring the amount of the first detection reagent and the second detection reagent bound to the binding surface(s).

Advantageously, the measurement step (i.e., the step involving the measurement of the first and second detection reagents (e.g., step (e)) may occur in a single volume or measurement chamber.

Measured, as used herein, is understood to encompass quantitative and qualitative measurement, and encompasses measurements carried out for a variety of purposes including, but not limited to, detecting the presence of an analyte, quantitating the amount of an analyte, identifying a known analyte, and/or determining the identity of an unknown analyte in a sample. According to one embodiment, the amounts the first binding reagent and the second binding reagent bound to one or more binding surfaces, measured according to the methods of the invention, may be presented as a concentration value of the analytes in a sample, i.e., the amount of each analyte per volume of sample.

In another embodiment of a solid phase binding assay method for measuring analytes in a sample, a first dilution of the sample is contacted with one or more binding surfaces and an amount of the first analyte, or analytes, is immobilized on the binding surface(s). The first analyte immobilized on the binding surface is then bound by a first detection reagent. Then, a second dilution of the sample, having a smaller dilution factor than the first dilution, is contacted with the same binding surface(s) and an amount of the second analyte, or analytes, is immobilized on the binding surface(s). The second analyte immobilized on said binding surface(s) is then bound by a second detection reagent. The amounts of the first binding reagents and the second binding reagents bound to one or more binding surface(s) are measured, preferably after the binding surface(s) are contacted with the first and second dilutions, and more preferably simultaneously.

Accordingly, the invention includes a method for measuring analytes in a sample comprising:
  a) contacting the first dilution of the sample with one or more binding surfaces;
  b) immobilizing an amount of a first analyte on the binding surface(s);
  c) binding a first detection reagent to the first analyte immobilized on the binding surface(s);
  d) contacting a second dilution of the sample with one or more binding surfaces, where the second dilution is having a dilution factor less than the first dilution;
  e) immobilizing an amount of the second analyte on the binding surface(s);

f) binding a second detection reagent to the second analyte immobilized on the surface(s); and g) measuring amounts of the first detection reagent and the second detection reagent bound to the binding surface(s).

Advantageously, the measurement step (i.e., the step involving the measurement of the first and second detection reagents (e.g., step (g)) may occur in a single volume or measurement chamber.

The amount of bound first detection reagent will correlate with the concentration of the first analyte in the first dilution; the first analyte in the second dilution may also bind the binding surface(s) but will not lead to the binding of additional first detection reagent. The amount of bound second detection reagent will correlate with the sum of the concentrations of the second analyte in the first and second dilutions; when the dilution factor of the first dilution is much greater than the second dilution, this sum will be roughly equal to the concentration of the second analyte in the second dilution.

The invention also includes a solid phase binding assay method for measuring analytes in a sample in which a first dilution of a sample and a first detection reagent are contacted with one or more binding surfaces, either simultaneously or sequentially. In one embodiments that use a sandwich assay format, one or more of the binding surface(s) and the first detection reagent bind to a first analyte to form a sandwich complex. In an alternative embodiment that uses a competitive binding assay format, one or more of the binding surfaces bind the first analyte, while the first detection reagent competes with the first analyte for binding to the binding surface(s). In yet another alternative embodiment that uses a competitive binding assay format, the first binding reagent binds the first analyte, while one or more of the binding surfaces compete with the first analyte for binding to the first detection reagent. After contacting the binding surface(s) with the first dilution, the binding surface(s) are contacted with a second dilution of the sample and a second detection reagent, either simultaneously or sequentially. As described above for the first analyte, the binding surface(s) and second detection reagent may be designed/selected to measure the second analyte using sandwich or competitive immunoassay formats. The first detection reagent and the second detection reagent bound to the one or more binding surfaces are measured, preferably after contacting the binding surface(s) with both the first and second dilutions, and more preferably they are measured simultaneously.

Accordingly, the invention includes a method for measuring analytes in a sample comprising:

a) contacting the first dilution of the sample with one or more binding surfaces;

b) contacting the binding surface(s) with the first detection reagent;

c) contacting the second dilution of the sample with the binding surface(s), wherein the second dilution is having a dilution factor less than the first dilution;

d) contacting the binding surface(s) with the second detection reagent; and e) measuring the first detection reagent and the second detection reagent bound to the binding surface(s).

wherein i) the binding surface(s) and the first detection reagent bind the first analyte;

ii) the binding surface(s) binds the first analyte and the first detection reagent competes with the first analyte for the binding surface(s);

iii) the first binding reagent binds the first analyte and the binding surface(s) competes with the first analyte for binding to the first detection reagent;

and wherein iv) the binding surface(s) and the second detection reagent bind the second analyte;

v) the binding surface(s) binds the second analyte and the second detection reagent competes with the second analyte for the binding surface(s);

vi) the second binding reagent binds the second analyte and the binding surface(s) competes with the second analyte for binding to the second detection reagent.

Advantageously, the measurement step (i.e., the step involving the measurement of the first and second detection reagents (e.g., step (e)) may occur in a single volume or measurement chamber.

According to certain embodiments of the invention, the first detection reagent is removed from the one or more binding surfaces prior to contacting these surfaces with the second dilution of the sample. The step of removing the first detection reagent may include washing the one or more binding surfaces with a washing reagent. Suitable washing procedures will be apparent to one of average skill in the art of solid phase binding assays. In the case of binding surfaces present on particles, removal of detection reagent and/or washing may include collecting the particles (e.g., by centrifugation, settling, filtration, use of a magnetic field, etc.) and removing the bulk fluid from the collected particles (e.g., by filtration or aspiration, etc.).

According to other embodiments of the invention, after the one or more binding surfaces have been contacted with the first dilution of the sample, but prior to contacting the surface(s) with the second dilution of the sample, unbound sites for the first analyte on the one or more binding surfaces are blocked to prevent binding, to the surface(s), of first analyte present in the second dilution. Preferred blocking agents bind to these unbound sites but do not bind with detection reagents, in particular, the first detection reagent. Suitable blocking agents include analogs of an analyte that are selected/engineered to have the moiety/epitope that binds to the binding surface(s) and not have the moiety/epitope that binds the first detection reagent. Specific examples include i) a fragment of nucleic acid analytes that omit a complementary sequence to a detection nucleic acid and ii) a fragment of a protein analyte (e.g., made by proteolysis, by de novo peptide synthesis or using recombinant DNA techniques) that omits the epitope bound by a detection antibody. Other examples will be readily apparent to a skilled practitioner. The use of a blocking agent may be combined with the step of removing the first detection reagent as described above (e.g., in one example, the blocking agent may be added to a wash reagent).

The term binding surface encompasses a wide range of solid phase supports including solid phase supports known in the art of solid phase binding assays. The binding surfaces may be formed on the surface of a variety of structures, such as electrodes, wells of a multi-well plate, beads or microparticles (including magnetic microparticles and latex microparticles), cuvettes, glass or polymer slides, porous membranes, gels, chips, tubes, etc.

Suitable materials for solid phase supports include, but are not limited to, glass, ceramic, polymer, polymer composite, and metal surfaces. Many suitable surface materials will be readily apparent to one of average skill in the art of solid phase assays. A variety of different textured surfaces may be used including flat surfaces and rough surfaces. In one embodiment, the surface is an electrode surface, e.g., an electrode surface within a multi-well plate, a flow cell or a flow cell chamber of a cartridge. Surfaces that are rough and/or suitable for use as electrodes are provided for by using a surface that comprises a material comprising elemental carbon, preferably a composite material containing particulate carbon in a matrix, e.g., a carbon ink.

Preferably, the binding surfaces may comprise at least one binding reagent immobilized thereon. The binding reagent may bind to an analyte of interest or compete with the analyte for binding a binding partner of the analyte. The binding of the analyte of interest to the binding reagent on the surface may be direct or may occur via one or more bridging reagents. Accordingly, the assay methods of the invention may include contacting the sample with a bridging reagent that binds both the binding reagent immobilized on the binding surface and an analyte.

The binding surfaces of the invention may comprise two or more discrete binding domains having one binding reagent specific to one analyte immobilized on one domain. In certain embodiments, the binding surfaces comprise at least two discrete binding domains, a first binding domain comprising first binding reagents that binds a first analyte and a second binding domain comprising second binding reagents that binds a second analyte. The binding domains may be patterned on a binding surface (e.g., as a patterned array of binding domains). Alternatively, the binding domains may be distributed among a plurality of particles. By way of example, a first binding domain may be on a first particle (or set of particles) and a second binding domain on a second particle (or set of particles).

Examples of array-based and particle based multiplexed assay systems that can be used with the methods of the invention include, but are not limited to, U.S. patent application Ser. Nos. 10/185,274 and 10/185,363, both filed on Jun. 28, 2002, entitled "Assay Plates, Reader Systems and Methods For Luminescence Test Measurements," published as U.S. Publ. No. 20040022677, U.S. patent application Ser. No. 10/238,960, filed Sep. 10, 2002, entitled "Methods, Reagents, Kits and Apparatus for Protein Function," published as US Pat. Pub. No. 20030207290, U.S. patent application Ser. No. 10/238,391, filed Sep. 10, 2002, entitled "Methods and apparatus for conducting multiple measurements on a sample"; published as US Pat. Publ. No. 20030113713, Provisional U.S. Patent Application No. 60/517,606, filed on Nov. 4, 2003, entitled "Modular Assay Plates, Reader System and Methods For Test Measurements"; and U.S. patent application Ser. No. 10/744,726, filed on Dec. 23, 2003, entitled "Assay Cartridges and Methods of Using Same," Fulton, R. J., R. L. McDade, P. L. Smith, L. J. Kienker, and J. R. Kettman Jr., Advanced multiplexed analysis with the FlowMetrix™ system, *Clinical Chemistry*, (1997) 43: 1749-1756, Joos, T. O., D. Stoll, and M. F. Templin, Miniaturised multiplexed immunoassay, *Current Opinion in Chemical Biology*, (2002) 6: 76-80, Vignali, D. A, Multiplexed particle-based flow cytometric assays, *Journal of Immunological Methods*, (2000) 243: 243-255, Yingyongnarongkul, B. E., S. E. How, J. J. Diaz-Mochon, M. Muzerelle, and M. Bradley, Parallel and multiplexed bead-based assays and encoding strategies, *Comb Chem High Throughput Screen*, (2003) 6: 577-587; each of which is incorporated by this reference.

Binding reagents that can be used as detection reagents, the binding components of binding surfaces and/or bridging reagents include, but are not limited to, antibodies, receptors, ligands, haptens, antigens, epitopes, mimitopes, aptamers, hybridization partners, and intercalaters. Suitable binding reagent compositions include, but are not limited to, proteins, nucleic acids, drugs, steroids, hormones, lipids, polysaccharides, and combinations thereof. The term "antibody" includes intact antibody molecules (including hybrid antibodies assembled by in vitro re-association of antibody subunits), antibody fragments and recombinant protein constructs comprising an antigen binding domain of an antibody (as described, e.g., in Porter, R. R. and Weir, R. C. *J. Cell Physiol.*, 67 (Suppl 1); 51-64 (1966) and Hochman, J. Inbar, D. and Givol, D. *Biochemistry* 12: 1130 (1973), hereby incorporated by reference). The term also includes intact antibody molecules, antibody fragments and antibody constructs that have been chemically modified, e.g., by the introduction of a label.

The detection reagents of the invention may be measured by measuring an intrinsic characteristic of the reagent such as color, luminescence, radioactivity, magnetic field, charge, refractive index, mass, chemical activity, etc. Alternatively, the detection reagent may be labeled with a detectable label and measured by measuring a characteristic of the label. Suitable labels include, but are not limited to, labels selected from the group consisting of ECL labels, luminescent labels, fluorescent labels, phosphorescent labels, radioactive labels, enzyme labels, electroactive labels, magnetic labels and light scattering labels.

In one embodiment of the invention the first detection reagent is labeled with a first label and the second detection reagent is labeled with the second label, wherein, the first and second labels are measurably distinct. "Measurably distinct", as understood herein, refer to labels that possess distinct identifiable and/or deconvolutable physical or chemical characteristics. The differences in these characteristics allow the labels to be independently measured in each others presence. These differences may include, but are not limited to, spectral differences in absorption or emission spectra, differences in conditions needed to induce chemiluminescence or electrochemiluminescence, differences in emission properties such as life time and polarization, differences in light scattering properties, differences in magnetic properties, differences in the energy of radioactive emissions, differences in the susceptibility to oxidation or reduction, etc.

One of ordinary skill in the art will be able to readily select detection technologies suitable for use with the methods of the invention. These detection technologies include, but are not limited to, a variety of methods that are currently available for measuring reactions (e.g., for measuring enzymatic reactions or binding reactions). Some techniques allow for measurements to be made by visual inspection, others may require or benefit from the use of an instrument to conduct the measurement. Techniques for measuring analytes may include coupling a reaction of the analyte (e.g., an enzyme catalyzed reaction) to a change in optical absorbance, fluorescence, chemiluminescence, electrical current, electrical potential, etc. Techniques available for measuring binding assays include solid phase binding assay techniques in which binding reaction products are formed on a surface and homogenous binding assay techniques in which binding reaction products remain in solution. Suitable detection techniques may detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques may be used that do not require the use of labels, e.g., techniques based on measuring mass (e.g., surface acoustic wave measurements), refractive index (e.g., surface plasmon resonance measurements), or the inherent luminescence of an analyte.

According to certain embodiments of the invention, analytes are detected using electrochemiluminescence-based assay formats. Electrochemiluminescence measurements are preferably carried out using binding reagents immobilized or otherwise collected on an electrode surface. Especially preferred electrodes include screen-printed carbon ink electrodes which may be patterned on the bottom of specially designed cartridges or multi-well plates (e.g., 24-, 96-, 384- etc. well plates). Electrochemiluminescence from ECL labels on the surface of the carbon electrodes is induced and measured using an imaging plate reader as described in copending U.S. application Ser. Nos. 10/185,274 and 10/185,363 (both entitled "Assay Plates, Reader Systems and Methods for Luminescence Test Measurements", filed on Jun. 28, 2002, hereby incorporated by reference). Analogous plates and plate readers are now commercially available (MULTI-SPOT® and MULTI-ARRAYT™ plates and SECTOR™ instruments, Meso Scale Discovery, a division of Meso Scale Diagnostics, LLC, Gaithersburg, Md.).

Examples of samples that may be analyzed include, but are not limited to, food samples, beverages, samples that comprise suspensions of dirt, environmental sludges or other environmental samples (such as suspensions of particles filtered, or otherwise concentrated, out of air samples, water samples, environmental swipes, etc.), and biological samples. Biological samples that may be analyzed include, but are not limited to, feces, mucosal swabs, physiological fluids and/or samples containing suspensions of cells. Specific examples of biological samples include blood, serum, plasma, tissue aspirates, tissue homogenates, cell cultures and cell culture supernatants (including cultures of eukaryotic and prokaryotic cells), urine, and cerebrospinal fluid.

The invention is further illustrated by the following examples.

EXAMPLES

The following examples are illustrative of some of the methods and instrumentation falling within the scope of the present invention. They are, of course, not to be considered in any way limitative of the invention. Numerous changes and modifications can be made with respect to the invention by one of ordinary skill in the art without undue experimentation.

Materials & Methods:

Markers:

Mouse adiponectin, insulin and leptin were purchased from MBL International, Kamiya and Antigenix America, respectively.

Marker Antibodies:

Capture antibodies for leptin (Cell Sciences, CPO001, Polyclonal from rabbit), insulin (Research Diagnostics, RDI-TRK2IP10-D3E7, Monoclonal) and adiponectin (RnD Systems, MAB1119, Monoclonal) and detection antibodies for leptin (R&D Systems, AF498, Polyclonal) insulin (Biogenesis, 5330-3339 Clone 5E4/3, Monoclonal) and adiponectin (RnD Systems, AF1119, Polyclonal) were obtained commercially. The detection antibodies were labeled with Sulfo-TAG NHS Ester (Meso Scale Discovery, Gaithersburg, Md.), an electrochemiluminescent label based on a sulfonated derivative of ruthenium-tris-bipyridine (compound 1 pictured below). Labeled antibodies were purified by size exclusion chromatography on Sephadex G-50 (Pharmacia Biosciences).

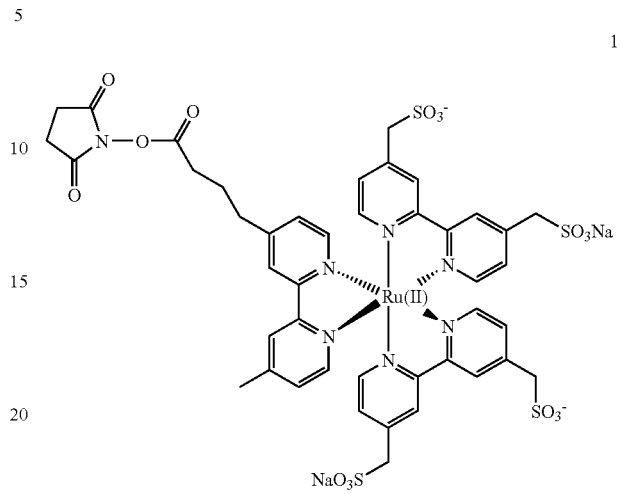

Multi-Well Plates for Electrochemiluminescence Measurements:

Electrochemiluminescence measurements were carried out using 4-spot, 96-well multi-well plates having integrated carbon ink electrodes for carrying out electrochemiluminescence measurements (Multi-Spot™ plates, Meso Scale Discovery, a division of Meso Scale Diagnostics, LLC, Gaithersburg, Md.). Each well had a carbon ink working electrode with four measurement regions ("spots") defined as apertures in a dielectric layer patterned over the working electrode. A patterned array of the three capture antibodies was prepared in each well by coating three of the spots with the three different capture antibodies. The spots were coated by passive adsorption of the antibodies from microdrops of antibody solution (250 nl at 300 ug/ml) that were microdispensed onto the spots. The fourth spot was coated with BSA and used as a negative control.

Electrochemiluminescence Measurement Instrument:

Electrochemiluminescence was induced and measured in the MULTI-SPOT plates using a SECTOR imager (Meso Scale Discovery, a division of Meso Scale Diagnostics, LLC, Gaithersburg, Md.).

Example 1

Multiplexed Assay for Mouse Adiponectin, Insulin and Leptin

Eight cocktail mixtures of insulin, leptin and adiponectin were prepared that covered the range of expected concentrations of these analytes in mouse serum and were used to simulate undiluted mouse serum samples. The concentration of adiponectin in the more concentrated cocktails is high enough so that 20 uL of undiluted sample can saturate all the adiponectin binding sites in the coated Multi-Spot plates described above. The concentrations of insulin and leptin are much lower and do not saturate their respective binding sites under the same conditions. For each cocktail sample, a matched diluted adiponectin sample was prepared (See, Table 1) that had a concentration of adiponectin equal to roughly a 1 in 220 dilution of the corresponding cocktail sample and was used to simulate diluted mouse serum samples.

Each of the dilute mouse adiponectin samples was mixed one-to-one (20 ul each) with its detection antibody (1 ug/ml, ~1 label per protein molecule) in a well of a 4-spot, 96-well Multi-Spot plate (having an array of antibodies against adiponectin, insulin and leptin as described above), and incubated for 2 hrs at room temperature. The plate was washed with PBS following the incubation. To each well was then added 20 uL of the corresponding undiluted cocktail sample and 20 uL of a mixture of the insulin detection antibody (0.5 ug/ml, ~8 labels per protein molecule) and the leptin detection antibody (0.5 ug/ml, ~5 labels per protein molecule) and the plates were incubated for an additional 2 hrs. The plate was washed with PBS, the wells were filled with 150 uL of MSD read buffer (Meso Scale Discovery) and the plates were analyzed on a Sector HTS plate reader.

TABLE 1

| Sample Pair | Adiponectin (pg/ml) | Cocktail Adiponectin (pg/ml) | Insulin (pg/ml) | Leptin (pg/ml) |
|---|---|---|---|---|
| 1 | 100,000 | 2,222,000 | 5,000 | 30,000 |
| 2 | 33,333 | 741,000 | 1,667 | 10,000 |
| 3 | 11,111 | 247,000 | 556 | 3,333 |
| 4 | 3,702 | 82,000 | 185 | 1,111 |
| 5 | 1,235 | 27,000 | 62 | 370 |
| 6 | 412 | 9,000 | 21 | 123 |
| 7 | 137 | 3,000 | 7 | 41 |
| 8 | 46 | 1,000 | 2.3 | 4 |

The measured ECL counts for each sample pair are representative of the concentration of insulin and leptin present during the second incubation step but the concentration of adiponectin present during the first incubation step (since this is the step during which adiponectin detection antibodies were present). The average of eight independent measurements was reported in FIG. 1. The experiment demonstrates that analytes of widely varying abundance can be measured in the same well using a single multiplexed assay that utilizes the two-tier incubation format.

Incorporation of References

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. A method for measuring analytes in a sample, the method comprising:
a) contacting a first dilution of said sample with one or more binding surfaces having binding reagents that bind a first analyte and a second analyte, wherein said one or more binding surfaces are located within a measurement chamber;
b) contacting said binding surface(s) with a first detection reagent, wherein said first detection reagent binds to said first analyte;
c) contacting a second dilution of said sample with said binding surface(s) in said measurement chamber, said second dilution having a dilution factor less than said first dilution;
d) contacting said binding surface(s) with a second detection reagent, wherein said second detection reagent binds to said second analyte; and
e) measuring the amount of said first detection reagent and said second detection reagent bound to said binding surface(s).

2. A method for measuring analytes in a sample, the method comprising:
a) contacting a first dilution of said sample with one or more binding surfaces in a measurement chamber;
b) contacting said binding surface(s) in said measurement chamber with a first detection reagent;
c) contacting a second dilution of said sample with said binding surface(s) in said measurement chamber, said second dilution having a dilution factor less than said first dilution;
d) contacting said binding surface(s) in said measurement chamber with a second detection reagent; and
e) measuring the amount of said first detection reagent and said second detection reagent bound to said binding surface(s)
wherein
i) said binding surface(s) and said first detection reagent bind said first analyte;
ii) said binding surface(s) binds said first analyte and said first detection reagent competes with said first analyte for said binding surface(s);
iii) said first binding reagent binds said first analyte and said binding surface(s) competes with said first analyte for binding to said first detection reagent;
and wherein
i) said binding surface(s) and said second detection reagent bind said second analyte;
ii) said binding surface(s) binds said second analyte and said second detection reagent competes with said second analyte for said binding surface(s);
iii) said second binding reagent binds said second analyte and said binding surface(s) competes with said second analyte for binding to said second detection reagent.

3. The method of claims 1 or 2, wherein said one or more binding surfaces comprises two discrete binding domains, a first binding domain comprising a first binding reagent that binds said first analyte and a second binding domain comprising a second binding reagent that binds said second analyte.

4. The method of claims 1 or 2, wherein the concentration of said first analyte in said sample is higher than the concentration of said second analyte.

5. The method of claims 1 or 2, wherein said sample is diluted in said first dilution by a factor of 10.

6. The method of claims 1 or 2 further comprising washing said first detection reagent from said binding surface(s) prior to contacting said binding surface(s) with said second dilution of said sample.

7. The method of claims 1 or 2 further comprising blocking unbound sites for said first analyte on said binding surface(s) after contacting said binding surface(s) with said first dilution of said sample but prior to contacting said binding surface(s) with said second dilution of said sample.

8. The method of claim 2, wherein said binding surface(s) has at least one binding reagent immobilized thereon.

9. The method of claim 8, wherein said binding reagent binds said analyte of interest.

10. The method of claim 9, further comprising contacting said sample with a bridging reagent that binds said binding reagent and said analyte.

11. The method of claims 1 or 2, wherein said binding surface(s) is an electrode surface(s).

12. The method of claims 1 or 2, wherein said binding surface(s) is an electrode surface(s) on the bottom of a multi-well plate.

13. The method of claims 1 or 2, wherein said binding surface(s) is a surface of a particle(s).

14. The method of claims 1 or 2, wherein said binding surface(s) is a surface of a magnetic particle(s).

15. The method of claims 1 or 2, wherein said binding surface(s) is a surface in a well(s) of a multi-well ELISA plate.

16. The method of claims 1 or 2, wherein said binding surface(s) is a surface of a glass slide.

17. The method of claims 1 or 2, wherein said first and second detection reagents are labeled with a label.

18. The method of claims 17, wherein said first detection reagent is labeled with a first label and said second detection reagent is labeled with a second label, and said first label and said second label are measurably distinct.

19. The assay of claim 18, wherein said label is selected from a group comprising ECL label, luminescent label, fluorescent label, phosphorescent label, radioactive label or light scattering label.

20. The method of claims 1 or 2, wherein said amounts of said first and second detection reagents are measured simultaneously.

* * * * *